United States Patent [19]

Nakanishi et al.

[11] Patent Number: 5,011,953
[45] Date of Patent: Apr. 30, 1991

[54] METHOD FOR PREPARING EPICHLOROHYDRINS

[75] Inventors: Takehisa Nakanishi, Takaishi; Eiji Koga, Izumi; Isao Fukada, Takaishi, all of Japan

[73] Assignee: Mitsui Toatsu Chemicals, Incorporated, Tokyo, Japan

[21] Appl. No.: 433,118

[22] Filed: Nov. 8, 1989

[30] Foreign Application Priority Data

Nov. 9, 1988 [JP] Japan ................................ 63-281349
Feb. 7, 1989 [JP] Japan .................................... 1-26579

[51] Int. Cl.$^5$ ............................................ C07D 301/19
[52] U.S. Cl. ..................... 549/529; 549/531; 549/563
[58] Field of Search ....................... 549/529, 531, 563

[56] References Cited

U.S. PATENT DOCUMENTS

| 3,923,843 | 12/1975 | Wulff, II ........................... | 549/529 |
| 4,021,454 | 5/1977 | Wulff et al. ....................... | 549/529 |
| 4,876,372 | 10/1989 | Nakanishi et al. ................ | 549/529 |

FOREIGN PATENT DOCUMENTS 287347 10/1988 European Pat. Off. ............ 549/529
52-7908 1/1977 Japan .

OTHER PUBLICATIONS

Inoe, et al., *Chemical Abstracts* 87:135000s, "Epoxides," abstract of JP-77-07,908 (1977).
Wulff et al., *Chemical Abstracts* 77:48197m, "Catalysts for Manufacturing Oxiranes," (1972).

*Primary Examiner*—Richard L. Raymond
*Assistant Examiner*—M. W. Russell
*Attorney, Agent, or Firm*—Oblon, Spivak, McClelland, Maier & Neustadt

[57] ABSTRACT

Disclosed herein is a method for preparing epichlorohydrins by reacting allyl chlorides with an alkyl hydroperoxide in the presence of a modified catalyst formed by substituting specific substituents for 1 to 50% of the silanol groups of a catalyst having titanium atoms bound to a silicon dioxide carrier via oxygen atoms and having on the same carrier 1 to 6 silanol groups per square nanometer thereof.

29 Claims, 1 Drawing Sheet

METHOD FOR PREPARING EPICHLOROHYDRINS

BACKGROUND OF THE INVENTION (1) Field of the Invention

The present invention relates to a method for preparing epichlorohydrins from allyl chlorides and an alkyl hydroperoxide.

(2) Description of the Prior Art

As manufacturing techniques of epichlorohydrins, there are known the chlorohydrin process, the chlorination process of allyl alcohol and the peroxide process.

In the chlorohydrin process, an allyl chloride and a chlorohydrin are used as a raw material and as an oxidizing agent, respectively, and therefore the amount of chlorine used therein is too great. In the allyl alcohol process, raw materials are expensive.

In the peroxide process, tert-butyl hydroperoxide, ethylbenzene hydroperoxide, cumene hydroperoxide, hydrogen peroxide, a peracid, etc. are used as oxidizing agents. Exemplary cases where homogeneous catalysts are used in this process are disclosed in Japanese Patent Publication Nos.19609/'73 and 17649/'70. In this process, however, the recovery of the catalyst is intricate and difficult, since it is dissolved in the reaction product mixture. There is another technique for synthesizing epichlorohydrin in which epoxidation of propylene or allyl chloride is carried out with the aid of an alkyl hydroperoxide in the presence of a solid catalyst, and this synthetic technique is described in Japanese Patent Laid-Open No. 55609/'74, Japanese Patent Publication No. 30049/'75 and J. Catalysis, 31, P. 438 (1973). In these publications, the reaction is performed by using stable tert-butyl hydroperoxide as the hydroperoxide with 2,6-di-tert-butyl-4-methylphenol added as a stabilizer, so that epichlorohydrin is obtained in a selectivity of 73% (on the basis of the hydroperoxide). However, when ethylbenzene hydroperoxide is used, the selectivity is 55%, and in the case of using cumene hydroperoxide, the selectivity is no more than 8%.

In Japanese Patent Laid-Open No. 7908/'77, there is disclosed epoxidation of olefins by using a solid catalyst formed by esterifying a metal-silicon oxide with a primary or secondary aliphatic alcohol. The selectivity to the desired epoxy compound seems to be improved by using the catalyst, but no description is made with regard to epichlorohydrins. The use of the catalyst is effective in the epoxidation of propylene.

Japanese Patent Publication No. 40526/'79 discloses a process in which a titanium-silica catalyst is brought into contact with a silylating agent in the production of oxirane compounds by the reaction of hydroperoxides with olefins. Allyl chloride is also illustrated as a variation of the olefins used as the raw material, but no specific description is made with the synthesis of epichlorohydrins.

SUMMARY OF THE INVENTION

The present inventors have already found that in the epoxidation of allyl chlorides with an organohydroperoxide, the yield of epichlorohydrins (the molar amount of an epichlorohydrin formed per mole of a hydroperoxide used) can be markedly increased by using a catalyst having silanol groups on the same silicon dioxide carrier onto which titanium atoms are bound. In this case, however, the yield of epichlorohydrins is about 50 to 80% and it has been difficult to improve the yield further.

A first object of the present invention is to provide a catalyst in the presence of which the yield of epichlorohydrins exceeds 80% in the aforesaid epoxidation reaction.

A second object of the present invention is to provide a method of preventing the catalyst from activity reduction.

The present inventors have made intensive investigations with the aim of attaining the above objects and found that by using a modified catalyst having titanium atoms and silanol groups on its silicon dioxide carrier and formed by substituting various substituents for a portion of the silanol groups, and moreover by using the catalyst together with basic compounds of alkaline earth metals, the objects of the present invention can be attained. The present invention has been completed on the basis of these findings.

The catalyst of the present invention is more specifically defined as a catalyst having titanium atoms bound to a silicon dioxide carrier via oxygen atoms and also having on the same carrier 1 to 6 silanol groups per square nanometer thereof, 1 to 50% of the silanol groups being replaced with hydrocarbon groups, alkoxy groups, acyl groups, acyloxy groups, carbamoyloxy groups, amino groups or organosilyloxy groups.

BRIEF DESCRIPTION OF THE DRAWING

In the drawing, the abscissa represents the reaction time in a batch reaction while the ordinate indicates the difference between the theoretical yield ($=1$) of an epichlorohydrin based on a hydroperoxide and the actual yield ($=$[EP]t/[EP]theo) on a logarismic scale.

[EP]theo: yield of an epichlorohydrin on molar basis when a hydroperoxide is entirely consumed for the epoxidation reaction.

[EP]t: actual yield of the epichlorohydrin on molar basis after a lapse of time t in hour.

Line (a) represents the results when the modified catalyst was used, while line (b) shows those with the unmodified catalyst.

DETAILED DESCRIPTION OF THE INVENTION AND PREFERRED EMBODIMENTS

In the present invention, epichlorohydrins generically mean epichlorohydrin and a 2-alkylepichlorohydrin in which a hydrogen atom at the 2-position of epichlorohydrin is replaced with an alkyl group having 1 to 3 carbon atoms.

In the present invention, allyl chlorides generically mean allyl chloride and a 2-alkylallyl chloride in which a hydrogen atom at the 2-position of allyl chloride is replaced with an alkyl group having 1 to 3 carbon atoms. These allyl chloride and substituted allyl chlorides are used as raw materials for the respective corresponding epichlorohydrin and substituted epichlorohydrins.

In the present invention, an alkyl hydroperoxide means cumene hydroperoxide, ethylbenzene hydroperoxide, tert-butyl hydroperoxide or cyclohexyl hydroperoxide.

The unmodified catalyst, on the basis of which the modified catalyst of the present invention is prepared, is a catalyst which has titanium atoms bound to a silicon dioxide carrier via oxygen atoms and also has silanol groups on the same carrier.

This catalyst is generally prepared in the following manner:

(1) A titanium halide, an alkoxytitanium, a carbonyl compound of titanium, or the like is brought into contact with a silica hydrogel having a suitable surface area and a suitable surface concentration of silanol groups, and the resulting hydrogel is heated at a low temperature enough to leave the silanol groups thereon in an atmosphere of a non-reducing gas or an oxygen-containing gas.

(2) After silanol groups of a carrier are partially etherified with an alcohol or esterified with an acid, the above-mentioned titanium compound is supported on the carrier, and then the ether groups or ester groups are removed therefrom to reproduce the silanol groups on the surface of the carrier.

(3) After a silica carrier is dehydrated so that the surface of the carrier may have siloxane bonds, the above-mentioned titanium compound is supported thereon, and then the carrier is hydrated by a water vapor treatment to impart a necessary number of silanol groups to the surface thereof.

The silica hydrogel used herein may include those prepared by precipitation from an aqueous sodium silicate solutin by acids, by decomposition of silicates, by combustion of ethyl silicate, or by other procedures. The silica hydrogel incorporates silanol groups on the surface and has a specific surface area of 1 m$^2$/g or more, preferably 100 m$^2$/g or more, a pore diameter of 50 Å or more, preferably 100 Å or more and a pore volume of 0.01 ml/g or more, preferably 0.1 ml/g or more, the number of the silanol groups on the surface ranging from 1 to 6, preferably from 3 to 6 per square nanometer ($10^{-18}$ m$^2$) of the surface area.

Liquid titanium compounds are preferred on account of their easy usage, and hence titanium tetrachloride, an alkoxytitanium and the like are used. These titanium compounds may be impregnated directly in a silica hydrogel or alternatively impregnated in a silica hydrogel after diluting the titanium compound with a solvent such as a hydrocarbon or an alcohol.

To cause a silica hydrogel to support a titanium compound, the former is brought into contact with the latter in an innert gas atmosphere. Afterward, the solvent used with the titanium compound is removed by heating the silica hydrogel under atmospheric pressure or under reduced pressure. Subsequently, the silica hydrogel is further heated at a comparatively low temperature, preferably at a temperature in the range of 100° to 250° C. in an atmosphere of a non-reducing gas such as nitrogen, argon or carbon dioxide, or an oxygen-containing gas such as air, so that an unmodified catalyst can be prepared.

The time required for the heating treatment ranges from 0.5 to 10 hours, usually from 1 to 5 hours. The temperature and time for the heat treatment have a great influence on the number of the silanol groups on the carrier, and therefore these conditions are very important in the manufacture of the catalyst.

In the catalyst obtained in the above manner, titanium atoms are bound to silicon atoms via oxygen atoms. The concentration of titanium is 0.01 to 20 titanium atoms, preferably 0.5 to 9 titanium atoms per square nanometer of the specific surface area. In the case of the carrier having a specific surface area of 100 m$^2$/g, the number of 0.5 to 9 titanium atoms per square nanometer is comparable to a titanium supporting concentration of 0.4 to 7 wt%. The hydroperoxide is supposed to be activated when coordinated with the titanium atoms.

However, the raw material, for example, an allyl chloride, gives the hydroperoxide low selectivity to the desired epoxide so far as conventional catalysts are used, since the reactivity of the double bond is low due to the strong electronegativity of the chlorine atom.

Thus, an attempt was made to modify the silanol groups of the silanol-titanium catalyst obtained in the manner as described above. The surface reforming of silicon oxide powder and its surface characteristics are illustrated, for example, in Hyomen (Surface) Vol. 11, p. 591 (1973). However, no description is made there of the effects of the surface-reformed products on specific reactions. With the conventional reforming processes in view, the present inventors have made attempts to partially modify the silanol groups with various substituents, and found that modified catalysts obtained by replacing 1 to 50% of the silanol groups with hydrocarbon groups, alkoxy groups, acyl groups, acyloxy groups, carbamoyloxy groups, amino groups or organosilyloxy groups as the substituents have marked effects on the epoxidation of allyl chlorides with alkyl hydroperoxides.

As an exemplary hydrocarbon group used as the substituent, there may be mentioned a straight, branched or cyclic alkyl group which has 1 to 20 carbon atoms and may be replaced with one or more halogen atoms or aromatic groups, or an aromatic hydrocarbon group which has 6 to 12 carbon atoms and may be replaced with one or more halogen atoms. These groups may be introduced into an unmodified catalyst in the following manner: An unmodified catalyst is dried and then treated with thionyl chloride at a temperature ranging from room temperature to 200° C. to convert a portion of the surface silanol groups to chloride. The resulting catalyst is reacted at a temperature ranging from room temperature to 100° C. with an alkyl lithium or Grignard reagent containing the corresponding hydrocarbon group described above.

The modified catalyst so obtained is rendered hydrophobic on the surface, exhibits strong resistance to hydrolysis between the silicon atom and modified groups, and hence has a high activity.

Exemplary alkoxy groups (RO—) used as the substituents may include those in which R is a straight, branched or cyclic alkyl or aralkyl group having 1 to 20 carbon atoms. These alkoxy groups may be introduced into an unmodified catalyst by heating the catalyst together with the corresponding alcohol or phenol, preferably at the critical temperature of the alcohol or phenol. Where R is a methyl group, the catalyst may be methoxylated with diazomethane. The thus-obtained alkoxy group-modified catalyst is rendered hydrophobic on the surface. Although the resistance to hydrolysis between the silicon atom and alkoxy groups is weaker than that in the case of the hydrocarbon group substitution, the catalyst is more economical in view of the raw materials for the substituents and the substitution procedures of the two cases.

Where the substituents are acyl groups, their introduction may be carried out in the following manner: An unmodified catalyst is treated at a temperature ranging from room temperature to 200° C. with thionyl chloride to convert the silanol groups on the surface to chlorides. The resulting catalyst is brought into contact with metallic lithium or metallic sodium in a tetrahydrofuran solvent to form a silyl-lithium compound or silyl-sodium compound. This compound is then reacted with an acid chloride (acyl chloride), whereby the corresponding acyl groups can be introduced into the catalyst. Such modification with acyl groups increases the electronegativity of the silica carrier and also enhances the electropositivity (or positive charge) of the titanium, contributing to the activation of the catalyst.

When the substituents are acyloxy groups, they may be introduced into an unmodified catalyst by reacting the catalyst with a ketene, acid chloride or acid anhydride under heating. Since the by-produced hydrochloric acid or carboxylic acid causes a reduction in the selectivity to the epoxidation reaction, it is advisable to wash the resulting catalyst with a hexane solvent containing pyridine and thereafter dry it by heating at a temperature ranging from 100° C. to 200° C. under vacuum so as to thoroughly remove the by-produced acid. Thus, a satisfactory catalyst can be obtained. By introducing acyloxy groups, the same characteristics as obtained in the introduction of acyl groups can be obtained, but the electropositivity of the titanium atom is made larger.

Carbamoyloxy groups may be introduced into an unmodified catalyst by reacting the catalyst with an alkyl isocyanate or aromatic isocyanate at a temperature ranging from room temperature to 100° C. The introduction of carbomoyloxy groups may contribute to making the surface of the catalyst weakly hydrophobic.

The amino group-modified catalyst may be obtained by heating a carbamoyloxy group-introduced catalyst at 150° C. or above under vacuum to cause a decarboxylation reaction and thereby to convert it to the corresponding amino compound. Another method of introducing amino groups is to react the unmodified catalyst, whose surface has been converted to a chloride by reacting with thionyl chloride, with an alkyl amine, aralkyl amine or aromatic amine having 1 to 20 carbon atoms. At this time, the reaction may be conducted in the co-presence of a solvent such as pyridine. The introduction of amino groups may contribute to the removal of acidic points on the surface of the catalyst.

When the substituents are organosilyloxy groups, may be illustrated as their general formula. In the formula, $R^1$, $R^2$ and $R^3$ are individually a hydrogen atom, a halogen atom, an aromatic hydrocarbon group, an alkyl group which has 1 to 20 carbon atoms and may be replaced with one or more halogen atoms, an aryl group which has 6 to 12 carbon atoms and may be replaced with one or more halogen atoms, or an alkoxy, aralkyloxy or aryloxy group having 1 to 20 carbon atoms. These groups may be introduced into an unmodified catalyst by heating the catalyst with an alkyl chlorosilane, alkoxychlorosilane, dialkylsilazane or dialkoxysilane. The modified catalyst so obtained is rendered hydrophobic on the surface, exhibits strong resistance to hydrolysis between the silicon atom and organosilyloxy groups, and has a high activity.

The modification ratio of the surface silanol groups is important from the standpoint of the nature of the catalyst. This is because the hydroperoxide is activated by adsorption to the titanium atom while the allyl chloride is adsorbed to the silanol groups for their activation. Therefore, when the catalyst is calcined at such high temperatures as to reduce the number of the surface silanol groups or the surface modification is so complete that the surface silanol groups are eliminated, the activity of the catalyst is impaired and the reaction is obstructed substantially.

The ratio of surface modification is largely dependent on the kind of modifying groups. A smaller ratio of modification is preferred when bulky groups are used. With less bulky methyl groups, it is allowable to increase the modification ratio up to 50% for those catalysts having a high concentration of silanol groups on the surface. With any substituents, the modified catalyst whose modification ratio is less than 1% can not be expected to give a distinct effect over the corresponding unmodified catalyst.

In order to react an alkyl hydroperoxide with an allyl chloride in the presence of at least one of the catalysts of the present invention, the raw materials may be diluted with a solvent prior to the reaction. Suitable solvents may include ethyl benzene and cumene which are reaction raw materials for the production of the corresponding hydroperoxides, chlorine-based alkylated compounds, and methylphenylcarbinol, cyclohexanol and tert-butanol which are formed from the corresponding hydroperoxides. No particular limitation is imposed on the concentration of the hydroperoxide. However, any solvent having 5 to 90 wt% of hydroperoxide is commonly employed.

In the proportion of an allyl chloride to a hydroperoxide, it is desirable to use the allyl chloride in excess of the hydroperoxide. In general, the yield may be improved by using 2 moles or more, preferably 5 moles or more of an allyl chloride per mole of a hydroperoxide. However, an excessively high molar ratio of an allyl chloride causes the yield to reach a limit. Hence, a molar ratio of less than 50 is appropriate from an economical point of view.

The reaction may be either a batch reaction or a continuous reaction. The catalyst may be used in a state of either suspension or fixed bed.

The amount of the catalyst used is 0.01 wt% or more and preferably ranges from 0.05 to 30 wt% based on the hydroperoxide. The reaction temperature is generally in the range of 0° to 250° C., preferably in the range of 20° to 150° C. No particular restrictions are placed on the reaction pressure. Any reaction pressures under which the reaction system is kept liquid can be employed.

In the foregoing reaction in the presence of the catalyst of the present invention, it is possible to prolong the life of the catalyst significantly by the co-existence of a basic compound of an alkaline earth metal. The basic compound of an alkaline earth metal may include oxides, hydroxides, carbonates and organic acid salts of alkaline earth metals. The basic compound is a compound represented by the following formula MO, $M(OH)_2$, $M(OH)X$, $MCO_3$ or $MX_2$ wherein M represents an alkaline earth metal atom such as Be, Mg, Ca, Sr and Ba and X indicates a halogen atom such as Cl, Br and I or a monovalent organic acid group. The compound may contain its water of crystallization.

These basic compounds may be used singly or as a mixture of the two or more, or as a complex composition. They may also be supported on the modified catalyst of the present invention. Further, they may be used in the form of being supported on other carriers.

The amount of the basic compound used is 0.01 to 10 times by weight that of the modified catalyst used, and preferably is 0.1 to 3 times by weight because the effect lasts as long as the basic characteristics remain.

EXAMPLES

The present invention will be illustrated specifically by reference to the following examples.

Preparation of an unmodified catalyst (A)

At 25° C., 2,170 g of a 30 wt% aqueous sodium silicate solution was mixed with 27 wt% sulfuric acid, and reaction was then performed at a pH of 1.5 for 1.5 hours to obtain a silica sol, and the latter was allowed to stand for 1.5 hours, so that its gelation took place. The thus-obtained gel was washed with ammonia water having a pH of 10.5 at 80° C. and was successively washed with water repeatedly, until the Na content had reached a level of 0.05 wt% or less. Then, this gel was dried at 150° C. overnight to prepare a silica hydrogel.

This silica hydrogel had a surface area of 300 m$^2$/g and an average pore diameter of 140 Å, and according to its thermogravimetric analysis, the number of silanol groups on the surface thereof was 6.0 per square nanometer (2.7 mmols/g).

Sixty grams of this silica hydrogel was added to a mixed solution of 120 ml of ethanol and 2.38 g of titanium tetrachloride, and the mixture was then agitated for 30 minutes so that the silica hydrogel was impregnated with the titanium tetrachloride. The ethanol was distilled off from the gel under atmospheric pressure. The resulting gel was dried at 100° C. under a reduced pressure of 3 Torr for 1 hour and then heated at 200° C. for 2 hours in a stream of air to obtain an unmodified catalyst (A).

On the thus-obtained carrier, 0.42 titanium atom per square nanometer of its surface was supported (0.21 mmol/g). The number of the silanol groups on the surface was 4.7 per square nanometer.

EXAMPLE 1

Twenty grams of the unmodified catalyst (A) obtained as described above was fed in a glass-made 4-neck flask with an inner volume of 200 ml. The contents were heated up to 75° C. under moderate agitation, added dropwise with 2.4 g of thionyl chloride, and aged for 2 hours under heating. The gas thereby evolved was absorbed in an aqueous sodium hydroxide solution by way of a condenser. After completion of the reaction, the contents were raised up to 150° C. and heated for 2 hours in a stream of nitrogen to remove unreacted raw materials and substitute chlorine atoms for the silanol groups. Thus, a silica gel having its surface chlorinated was obtained. Its elementary analysis revealed that the substitution ratio by chlorine atoms was 32% of the silanol groups.

The silica gel having its surface chlorinated was added to 50 g of diisopropyl ether containing 0.66 g of methyl lithium and the mixture was agitated for 3 hours to effect methylation of the gel. Upon completion of the reaction, the silica gel which had been separated by filtration was washed with 50 g of ethyl ether and dried. This dried product was heated at 200° C. for 2 hours to prepare a methyl group-modified catalyst. Its elementary analysis clarified that the substitution ratio by methyl groups was 24% of the silanol groups.

Figure 1:
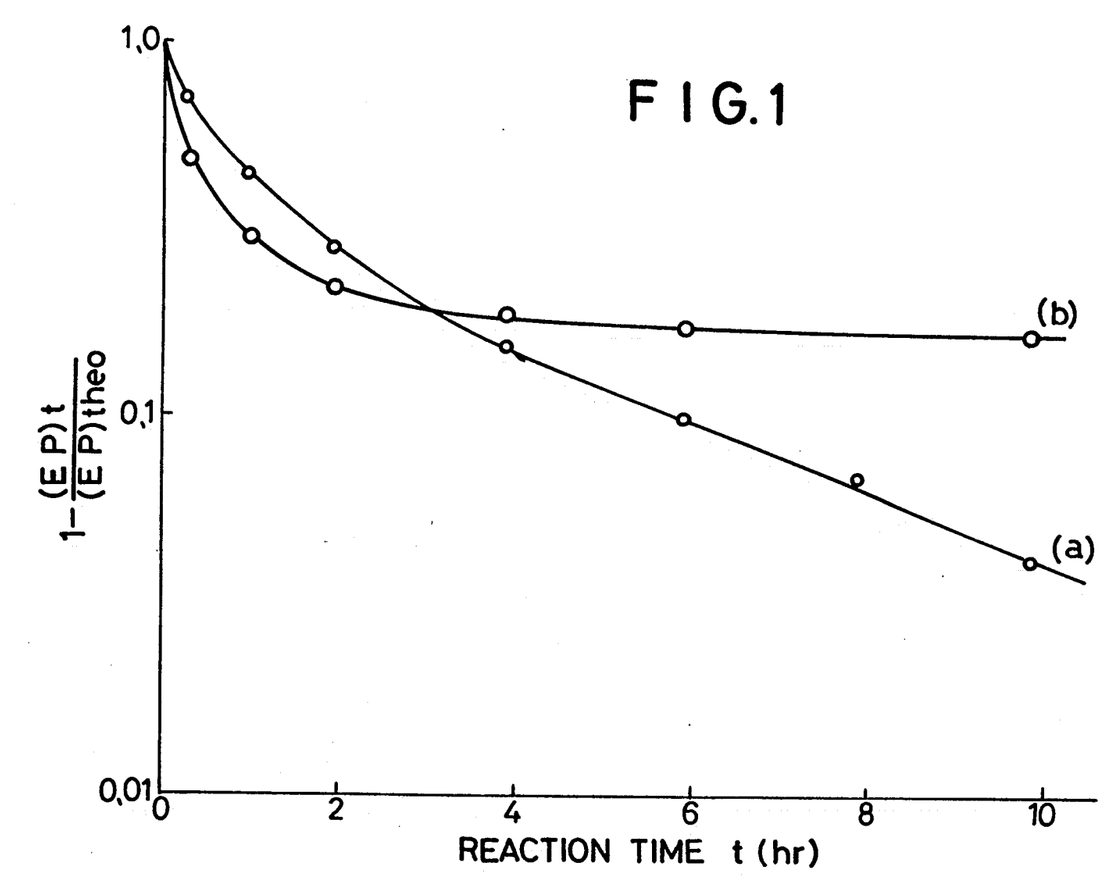
FIG. 1 is a drawing illustrating some examples of the relation between the reaction time and epichlorohydrin yield when a modified catalyst and an unmodified catalyst for use in the present invention are employed.

In an stainless steel autoclave with an inner volume of 300 ml were added 12.0 g of the methyl group-modified catalyst obtained in the foregoing preparation, 128.5 g of allyl chloride and 30.5 g of a cumene solution containing 40 wt% of cumene hydroperoxide to cause reaction at 40° C. for 10 hours. The concentration of the residual hydroperoxide in the reaction solution was determined by iodometry so that the conversion of the cumene hydroperoxide was calculated. The epichlorohydrin yield was determined from the analysis of the reaction solution by gas chromatography. The relation between the reaction time and epichlorohydrin yield is illustrated as line (a) in FIG. 1. As seen in FIG. 1, the yield of epichlorohydrins is observed to increase with the passage of reaction time.

COMPARATIVE EXAMPLE 1

Reaction was carried out in the same manner as in Example 1 except for the use of the unmodified catalyst (A) in place of the methyl group-modified catalyst. The relation between the reaction time and epichlorohydrin yield is shown as line (b) in FIG. 1. With the unmodified catalsyt, it is observed that the increase of epichlorohydrin yield suddenly reaches the top as the reaction time elapses.

EXAMPLE 2

Seventy grams of carbitol, 42.0 g of a 40 wt% aqueous potassium hydroxide solution and 20 ml of ethyl ether were charged in a 1000 ml flask, followed by dropwise addition under agitation of a solution formed by dissolving 43.0 g of p-tolylsulfonyl methylnitrosoamide in 280 ml of ethyl ether. The diazomethane evolved was passed through a flask in which 10.0 g of a previously-prepared unmodified catalyst (A) was suspended in 200 ml of ethyl ether to effect methoxylation of the catalyst. Following the reaction, the catalyst was heated at 200° C. for 2 hours in a stream of nitrogen to obtain a methoxylated modified catalyst. As a result of its elementary analysis, the substitution ratio by methoxy groups was 17% of the silanol groups.

To 12.0 g of the above methoxy group-modified catalyst were added 66 g of allyl chloride and 48.0 g of an ethylbenzene solution containing 25 wt% of ethylbenzene hydroperoxide. The resulting mixture was subjected to reaction at 90° C. for 2 hours. The results are given in Table 1.

COMPARATIVE EXAMPLE 2

Reaction was carried out in the same manner as in Example 2 except for the use of the unmodified catalyst (A) in place of the methoxy group-modified catalyst. The results are given in Table 1.

TABLE 1

| Time-dependent variation of epichlorohydrin yield (%) | | | | |
| --- | --- | --- | --- | --- |
| Reaction time (hr) | 0.5 | 1.0 | 1.5 | 2.0 |
| Example 2 | 50 | 73 | 82 | 88 |
| Comp. Example 2 | 65 | 73 | 76 | 77 |

EXAMPLE 3

The interior of a 500 ml autoclave containing 30.0 g of the unmodified catalyst (A) was evacuated, in which 100 ml of anhydrous ethanol was successively sucked.

Under moderate agitation, the contents were raised up to 240° C. over 1.5 hours. At this moment, the pressure rised to 65 kg/cm$^2$G. The valve was immediately opened to discharge the ethanol outside so that the pressure was releated to atmospheric, and then the valve was closed. The autoclave and immersed in a water bath and sucked for 4 hours under vacuum to remove the residual ethanol. Then, the catalyst so obtained was taken out of the autoclave, packed in a quartz tube, and heated at 200° C. for 2 hours in a stream of nitrogen to obtain an ethoxylated modified catalyst. As a result of its elementary analysis, the substitution ratio by ethoxy groups was 38% of the silanol groups.

To 7.5 g of the ethoxy group-modified catalyst were added 77.0 g of allyl chloride and 12.0 g of a toluene solution containing 75 wt% of tert-butyl hydroproxide, and the mixture was subjected to reaction at 40° C. for 10 hours. The results are given in Table 2.

COMPARATIVE EXAMPLE 3

Reaction was carried out in the same manner as in Example 3 except for the use of the unmodified catalyst (A) in place of the ethoxy group-modified catalyst. The results are given in Table 2.

TABLE 2

| Time-dependent variation of epichlorohydrin yield (%) | | | | |
|---|---|---|---|---|
| Reaction time (hr) | 1.0 | 2.0 | 5.0 | 10.0 |
| Example 3 | 40 | 57 | 74 | 88 |
| Comp. Example 3 | 65 | 75 | 78 | 79 |

EXAMPLE 4

A glass-made 4-neck flask with an inner volume of 300 ml, provided with an agitator, dropping funnel and gas inlet nozzle, was fully replaced with nitrogen. In the flask, 100 ml of tetrahydrofuran dehydrated by Molecular Sieve 5A and 0.4 g of metallic lithium were fed successively. Under agitation at room temperature, 20 g of a chlorinated catalyst, which had been obtained by treating the silanol groups on the surface of the unmodified catalyst (A) with thionyl chloride in the same manner as in Example 1, was added and the mixture was subjected to reaction for 6 hours at room temperature. The reaction liquid was added dropwise with 4.8 g catalyst chloride, followed by reaction at 65° C. for 3 hours under heating. Then, the catalyst obtained by filtration was washed twice with 100 ml of tetrahydrofuran, dried overnight under reduced pressure, and heated at 200° C. for 2 hours in a stream of nitrogen. As a result of the elementary analysis of the modified catalyst obtained, the substitution ratio by acetyl groups was 16% of the silanol groups.

In a stainless steel autoclave with an inner volume of 200 ml, 10.0 g of the acetyl group-modified catalyst obtained in the foregoing preparation, 50.0 g of allyl chloride and 40.0 g of an ethylbenzene solution containing 25 wt% of ethylbenzene hydroperoxide were added, and the mixture was subjected to reaction at 80° C. for 2 hours. The results are given in Table 3.

COMPARATIVE EXAMPLE 4

Reaction was carried out in the same manner as in Example 4 except for the use of the unmodified catalyst (A) in place of the acetyl group-modified catalyst. The results are given in Table 3.

TABLE 3

| Time-dependent variation of epichlorohydrin yield (%) | | | | |
|---|---|---|---|---|
| Reaction time (hr) | 0.5 | 1.0 | 1.5 | 2.0 |
| Example 4 | 43 | 64 | 77 | 82 |
| Comp. Example 4 | 51 | 67 | 72 | 73 |

Preparation of an unmodified catalyst (B)

At 25° C., 2,170 g of a 30 wt% aqueous sodium silicate solution was mixed with 27 wt% sulfuric acid, and reaction was then performed at a pH of 1.5 for 1.5 hours to obtain a silica sol, and the latter was allowed to stand for 1.5 hours, so that its gelation took place. The thus-obtained gel was washed with ammonia water having a pH of 10.5 at 80° C. and was successively washed with water repeatedly, until the Na content had reached a level of 0.05 wt% or less. Then, this gel was dried at 150° C. overnight to prepare a silica hydrogel. This silica hydrogel had a surface area of 300 m$^2$/g and an average pore diameter of 140 Å, and according to its thermogravimetric analysis, the number of the silanol groups on the surface was 6.0 per square nanometer (2.7 mmols/g).

In a 300 ml glass-made 4-neck flask were fed 100 g of the above silica hydrogel (20–40 mesh) and 200 ml of anhydrous ethanol (water content: 30 ppm). To the resulting mixture was added 9.5 g of ethyl orthotitanate under agitation so that the hydrogel was caused to support titanium at room temperature for 1 hour. After removing the ethanol by distillation at atmospheric pressure, the hydrogel was dried at 110° C. for 5 hours under reduced pressure and then heated at 200° C. for 2 hours in a stream of air to obtain an unmodified catalyst (B). The elementary analysis of the catalyst revealed that it carried 0.84 titanium atom per square nanometer of its surface (0.42 mmol/g). Its thermogravimetry clarified that the number of the silanol groups on the surface was 4 per square nanometer (1.8 mmols/g).

EXAMPLE 5

A quartz-made reaction tube (inner diameter: 15 mm, length: 300 mm), provided with a preheater precedingly, was heated to 600° C. in an electric furnace. While passing therethrough gaseous nitrogen at a rate of 40 ml/min, diketene was fed dropwise in the preheater at a rate of 0.1 ml/min. At the outlet of the quartz reaction tube was provided a trap cooled at −20° C., which collected unreacted diketene. A gaseous mixture of the ketene evolved and nitrogen was introduced in a 300 ml glass-made 4-neck flask, which had contained 50 g of the unmodified catalyst (B) and had been heated to 130° C., under moderate agitation over 2 hours. As a result of elementary analysis, the substitution ratio by acetoxyl groups was 29% of the silanol groups.

In a stainless steel autoclave with an inner volume of 200 ml, 10.0 g of the acetoxyl-group modified catalyst obtained in the foregoing preparation, 50.0 g of allyl chloride and 40.0 g of an ethylbenzene solution containing 25 wt% of ethylbenzene hydroperoxide were fed and the resulting mixture was subjected to reaction at 80° C. for 2 hours. The results are given in Table 4.

COMPARATIVE EXAMPLE 5

Reaction was carried out in the same manner as in Example 5 except for the use of the unmodified catalyst (B) in place of the acetoxyl group-modified catalyst. The results are given in Table 4.

TABLE 4

| Time-dependent variation of epichlorohydrin yield (%) | | | | | |
|---|---|---|---|---|---|
| Reaction time (hr) | 0.25 | 0.5 | 1.0 | 1.5 | 2.0 |
| Example 5 | 45 | 63 | 78 | 86 | 90 |
| Comp. Example 5 | 51 | 67 | 76 | 78 | 79 |

EXAMPLE 6

A solution formed by dissolving 10.1 g of phenyl isocyanate in 200 ml of benzene was fed in a 300 ml glass-made 4-neck flask provided with an agitator, which had previously contained 50.0 g of the unmodified catalyst (B), and the resulting mixture was heated at 80° C. for 3 hours at reflux with gentle agitation. Then, the solvent was removed and the catalyst was washed twice with 150 ml of benzene to remove unreacted phenyl isocyanate, followed by drying at 80° C. overnight under reduced pressure. The elementary analysis of the modified catalyst obtained revealed that the substitution ratio by N-phenylcarbamoyloxy groups was 22% of the silanol groups.

In a 200 ml stainless steel autoclave, 10.0 g of the above modified catalyst, 76.5 g of allyl chloride and 12.0 g of a toluene solution containing 75 wt% of tert-butyl hydroperoxide were fed and the resulting mixture was subjected to reaction at 80° C. for 2 hours under agitation. The results are given in Table 5.

COMPARATIVE EXAMPLE 6

Reaction was carried out in the same manner as in Example 6 except for the use of the unmodified catalyst (B) in place of the N-phenylcarbamoyloxy group-modified catalyst. The results are given in Table 5.

TABLE 5

| Time-dependent variation of epichlorohydrin yield (%) | | | | |
|---|---|---|---|---|
| Reaction time (hr) | 0.5 | 1.0 | 1.5 | 2.0 |
| Example 6 | 49 | 64 | 83 | 86 |
| Comp. Example 6 | 58 | 67 | 79 | 80 |

EXAMPLE 7

Twenty grams of a catalyst, obtained by substituting chlorine atoms for the silanol groups on the surface of the unmodified catalyst (A) by using thionyl chloride in the same manner as in Example 1 (substitution ratio: 32%), was fed in a 200 ml stainless steel autoclave. The interior of the autoclave was evacuated and then heated to 100° C. Under moderate agitation, 1.9 g of dimethyl amine was sucked in the autoclave and the contents were reacted for 4 hours. After completion of the reaction, gaseous nitrogen was passed through the autoclave while maintaining the temperature at 100° C. Then the autoclave was evacuated so as to remove unreacted dimethyl amine. The contents were heated at 200° C. for 2 hours in a stream of nitrogen to remove hydrochloric acid. As a result of the elementary analysis of the modified catalyst so obtained, the substitution ratio by amino groups was 22% of the silanol groups.

In a stainless steel autoclave with an inner volume of 200 ml were fed 10 g of the amino group-modified catalyst obtained in the foregoing preparation, 50.0 g of allyl chloride and 40.0 g of an ethylbenzene solution containing 25 wt% of ethylbenzene hydroperoxide, which were then reacted at 80° C. for 2 hours. The results are given in Table 6.

TABLE 6

| Time-dependent variation of epichlorohydrin yield (%) | | | | |
|---|---|---|---|---|
| Reaction time (hr) | 0.5 | 1.0 | 1.5 | 2.0 |
| Example 7 | 43 | 66 | 79 | 84 |
| Comp. Example 4 | 51 | 67 | 72 | 73 |

EXAMPLE 8

In a stainless steel autoclave with an inner volume of 200 ml was fed 30.0 g of the unmodified catalyst (B), and the autoclave was evacuated and then heated to 180° C. Under moderate agitation, 3.0 g of hexamethyl disilazane was sucked in the autoclave and the contents were reacted at 180° C. for 4 hours. Subsequently, the catalyst was taken out and heated at 200° C. for 2 hours in a stream of nitrogen. The elementary analysis of the modified catalyst thus-obtained elucidated that the substitution ratio by trimethylsilyl groups was 29% of the silanol groups.

In a stainless steel autoclave with an inner volume of 200 ml were added 12.0 g of the silyl group-modified catalyst obtained in the foregoing preparation, 64 g of allyl chloride and 30 g of a cumene solution containing 40 wt% of cumene hydroperoxide, which were then reacted at 40° C. for 10 hours. The results are given in Table 7.

COMPARATIVE EXAMPLE 8

Reaction was carried out in the same manner as in Example 8 except for the use of the unmodified catalyst (B) in place of the silyl group-modified catalyst. The results are given in Table 7.

TABLE 7

| Time-dependent variation of epichlorohydrin yield (%) | | | | |
|---|---|---|---|---|
| Reaction time (hr) | 2.0 | 4.0 | 6.0 | 10.0 |
| Example 8 | 67 | 82 | 88 | 94 |
| Comp. Example 8 | 73 | 77 | 78 | 80 |

EXAMPLE 9

In a stainless steel autoclave with an inner volume of 300 ml were added 12.0 g of the methyl group-modified catalyst used in Example 1, 152.0 g of methallyl chloride and 96.0 g of a cyclohexane solution containing 10.4 wt% of cyclohexyl hydroperoxide and the contents were subjected to reaction at 100° C. for 6 hours. The results are given in Table 8.

COMPARATIVE EXAMPLE 9

Reaction was carried out in the same manner as in Example 9 except for the use of the unmodified catalyst (A) in place of the methyl group-modified catalyst. The results are given in Table 8.

TABLE 8

| Time-dependent variation of epichlorohydrin yield (%) | | | | |
|---|---|---|---|---|
| Reaction time (hr) | 1.0 | 2.0 | 4.0 | 6.0 |
| Example 9 | 23 | 37 | 57 | 70 |
| Comp. Example 9 | 34 | 43 | 51 | 55 |

COMPARATIVE EXAMPLE 10

Twenty grams of the unmodified catalyst (A) was fed in a glass-made 4-neck flask with an inner volume of 200 ml and heated to 200° C. under moderate agitation. To the catalyst so heated was added dropwise 2.4 g of thionyl chloride, and the mixture was heated over 2 hours for aging. The unreacted starting material was removed in a stream of nitrogen so that a surface chlorinated catalyst was obtained. Its elementary analysis clarified that the substitution ratio of the silanol groups by chlorine atoms was 75%.

This surface chlorinated catalyst was added to 100 g of isopropyl ether containing 1.5 g of methyl lithium and the resulting mixture was agitated for 5 hours, whereby the catalyst was methylated. The methylated catalyst was heated at 200° C. for 2 hours in a stream of nitrogen to obtain a methyl group-modified catalyst with the substitution ratio of the silanol groups of 57%.

Using this catalyst, reaction was carried out over 10 hours in the same manner as in Example 1. The results are given in Table 9, together with the corresponding numerals of Comparative Example 1 and Example 1.

TABLE 9

| Time-dependent variation of epichlorohydrin yield (%) | | | | | |
|---|---|---|---|---|---|
| Reaction time (hr) | 0.5 | 1.0 | 2.0 | 4.0 | 10.0 |
| Comp. Example 1 | 49 | 69 | 77 | 80 | 81 |
| Example 1 | 26 | 54 | 71 | 84 | 95 |
| Comp. Example 10 | 8 | 11 | 19 | 32 | 60 |

As seen in Table 9, an increase in the surface treatment rate causes a reduction in the reaction yield.

COMPARATIVE EXAMPLE 11

In the preparation of the unmodified catalyst (A) in Example 1, following the impregnation of titanium, ethanol was removed by distillation, and the silica gel was dried at 100° C. and then heated at 800° C. for 2 hours in a stream of nitrogen. The catalyst thus-obtained supported 0.42 titanium atom per square nanometer of its carrier surface. The number of the silanol groups on the surface was 0.3 per square nanometer by the thermogravimetry.

This high-temperature calcined catalyst was ethoxylated at its surface in the same manner as in Example 3. As a result of its elementary analysis, the substitution ratio by ethoxy groups was 67% of the silanol groups.

To 7.5 g of the catalyst were added 77.0 g of allyl chloride and 12.0 g of a toluene solution containing 75 wt% of tert-butyl hydroperoxide, and the mixture was subjected to reaction at 40° C. for 10 hours. The results are given in Table 10.

TABLE 10

| Time-dependent variation of epichlorohydrin yield (%) | | | | |
|---|---|---|---|---|
| Reaction time (hr) | 1.0 | 2.0 | 5.0 | 10.0 |
| Comp. Example 11 | 10 | 14 | 21 | 30 |

EXAMPLE 10

In a stainless steel-made, outer-jacketed pressure-tight reactor with an inner diameter of 20 mm and a length of 300 mm (this reactor was used likewise hereunder) were packed 10 g of the methyl group-modified catalyst (20 mesh) obtained in Example 1 and 10 g of calcium oxide (size: 60 mesh, a 500° C. calcined product) in a uniformly dispersed state. A cumene solution containing 40 wt% of cumene hydroperoxide and allyl chloride (hereinafter referred to as ALC), at a weight ratio of the hydroperoxide to the ALC of 1 to 10.7, were charged into the reactor separately by pumps at a liquid hourly space velocity (hereinafter abbreviated as LHSV) of 0.3/hr per unit volume of the modified catalyst in terms of the sum of both starting liquids. Thus, they were reacted there at 40° C.

The concentration of the residual hydroperoxide in the reaction mixture was determined by iodometry to calculate the conversion of the cumene hydroperoxide and the epichlorohydrin yield was obtained from the analysis of the reaction mixture by gas chromatography. The relation between the reaction time and hydroperoxide (hereinafter abbreviated as HPO) conversion and the relation between the reaction time and epichlorohdyrin (hereinafter abbreviated as ECH) yield are shown in Table 11.

REFERENCE EXAMPLE 1

Reaction was carried out in the same manner as in Example 10 except for the use of the reactor packed only with the methyl group-modified catalyst obtained in example 1. The results are given in Table 11.

TABLE 11

| Reaction time (hr) | 100 | 300 | 700 |
|---|---|---|---|
| Example 10 | | | |
| HPO conversion % | 64 | 41 | 43 |
| ECH yield % | 58 | 47 | 40 |
| Ref. Ex. 1 | | | |
| HPO conversion % | 53 | 40 | 30 |
| ECH yield % | 48 | 37 | 27 |

EXAMPLE 11

In the reactor packed with a mixture of 10 g of the methoxy group-modified catalyst (20 mesh) obtained in Example 2 and 10 g of barium carbonate (30–60 mesh), an ethylbenzene solution containing 25 wt% of ethylbenzene hydroperoxide and ALC, at a weight ratio of the HPO to the ALC of 1 to 10, were charged at an LHSV of 1.0/hr, and reacted there at 90° C. The results are given in Table 12.

REFERENCE EXAMPLE 2

Reaction was carried out in the same manner as in Example 11 except that the barium carbonate was not used. The results are given in Table 12.

TABLE 12

| Reaction time (hr) | 120 | 360 | 720 |
|---|---|---|---|
| Example 11 | | | |
| HPO conversion % | 81 | 76 | 68 |
| ECH yield % | 69 | 65 | 58 |
| Ref. Ex. 2 | | | |
| HPO conversion % | 66 | 61 | 51 |
| ECH yield % | 55 | 50 | 43 |

EXAMPLE 12

In the reactor packed with a mixture of 10 g of the ethoxy group-modified catalyst obtained in Example 3 and 10 g of crushed calcium carbonate, a toluene solution containing 75 wt% of tert-butyl hydroperoxide and ALC, at a weight ratio of the HPO to the ALC of 1 to 5, were charged at an LHSV of 0.3/hr, and reacted there at 40° C. The results are given in Table 13.

REFERENCE EXAMPLE 3

Reaction was carried out in the same manner as in Example 12 except that the crushed calcium carbonate was not used. The results are given in Table 13.

TABLE 13

| Reaction time (hr) | 100 | 300 | 700 |
|---|---|---|---|
| Example 12 | | | |
| HPO conversion % | 50 | 40 | 34 |
| ECH yield % | 45 | 36 | 31 |
| Ref. Ex. 3 | | | |
| HPO conversion % | 41 | 31 | 26 |
| ECH yield % | 37 | 28 | 23 |

EXAMPLE 13

Into 500 ml of anhydrous ethanol contained in a 1000 ml glass flask, 1 g of barium hydroxide was added and dissolved under heating. Then, 20 g of the acetyl group-modified catalyst obtained in Example 4 was added to the resulting solution. The solvent was removed by distillation while mixing by means of a rotary evaporator. The resulting solid was heated at 200° C. for 2 hours in a stream of nitrogen to obtain a supported catalyst. In the reactor was packed 10 g of the supported catalyst obtained and reaction was conducted in the same manner as in Example 11 except for the alteration in reaction temperature to 80° C. and in LHSV to 0.5/hr. The results are given in Table 14.

REFERENCE EXAMPLE 4

Reaction was carried out in the same manner as in Example 13 except for the use of the acetyl group-modified catalyst obtained in Example 4 in place of the supported catalyst. The results are given in Table 14.

TABLE 14

| Reaction time (hr) | 120 | 360 | 720 |
|---|---|---|---|
| Example 13 | | | |
| HPO conversion % | 91 | 82 | 70 |
| ECH yield % | 80 | 72 | 61 |
| Ref. Ex. 4 | | | |
| HPO conversion % | 83 | 70 | 49 |
| ECH yield % | 74 | 63 | 44 |

EXAMPLE 14

Reaction was carried out in the same manner as in Example 13 except that a mixture of 10 g of the acetoxyl group-modified catalyst obtained in Example 5 and 10 g of granular magnesium hydroxide was packed in the reactor. The results are given in Table 15.

REFERENCE EXAMPLE 5

Reaction was carried out in the same manner as in Example 14 except that the granular magnesium hydroxide was not used. The results are given in Table 15.

TABLE 15

| Reaction time (hr) | 120 | 360 | 720 |
|---|---|---|---|
| Example 14 | | | |
| HPO conversion % | 92 | 83 | 72 |
| ECH yield % | 83 | 75 | 65 |
| Ref. Ex. 5 | | | |
| HPO conversion % | 84 | 71 | 52 |
| ECH yield % | 76 | 64 | 47 |

EXAMPLE 15

In the reactor packed with a mixture of 10.0 g of the n-phenylcarbamoyloxy group-modified catalyst obtained in Example 6 and 5 g of granular strontium oxide, a toluene solution containing 75 wt% of tert-butyl hydroperoxide and ALC, at a weight ratio of the HPO to the ALC of 1 to 10, were charged at an LHSV of 0.5/hr, and reacted there at 80° C. The results are given in Table 16.

REFERENCE EXAMPLE 6

Reaction was carried out in the same manner as in Example 15 except that the strontium oxide was not used. The results are given in Table 16.

TABLE 16

| Reaction time (hr) | 100 | 200 | 400 |
|---|---|---|---|
| Example 15 | | | |
| HPO conversion % | 88 | 85 | 72 |
| ECH yield % | 75 | 72 | 62 |
| Ref. Ex. 6 | | | |
| HPO conversion % | 85 | 77 | 62 |
| ECH yield % | 72 | 65 | 53 |

EXAMPLE 16

In the reactor packed with a mixture of 10.0 g of the amino group-modified catalyst obtained in Example 7 and 10 g of a crushed product of dolomite ($MgCO_3$.-$CaCO_3$ composition), an ethylbenzene solution containing 25 wt% of ethylbenzene hydroperoxide and ALC, at a weight ratio of the HPO to the ALC of 1 to 5, were charged at an LHSV of 0.5/hr, and reacted there at 80° C. The results are shown in Table 17.

REFERENCE EXAMPLE 7

Reaction was carried out in the same manner as in Example 16 except that the crushed product of dolomite ($MgCO_3$.$CaCO_3$ composition) was not used. The results are given in Table 17.

TABLE 17

| Reaction time (hr) | 100 | 200 | 400 |
|---|---|---|---|
| Example 16 | | | |
| HPO conversion % | 74 | 72 | 65 |
| ECH yield % | 65 | 63 | 57 |
| Ref. Ex. 7 | | | |
| HPO conversion % | 75 | 63 | 42 |
| ECH yield % | 68 | 67 | 37 |

EXAMPLE 17

In the reactor in which 10 g of the silyl group-modified catalyst obtained in Example 8 and 10 g of granular magnesium hydroxide had been packed, a cumene solution containing 40 wt% of cumene hydroperoxide and ALC, at a weight ratio of the HPO to the ALC of 1 to 10, were charged separately by pumps at an LHSV of 0.3 /hr, and reacted there at 40° C. The results are given in Table 18.

REFERENCE EXAMPLE 8

REaction was carried out in the same manner as in Example 17 except that the granular magnesium hydroxide was not used. The results are given in Table 18.

TABLE 18

| Reaction time (hr) | 100 | 300 | 700 |
|---|---|---|---|
| Example 17 | | | |
| HPO conversion % | 72 | 66 | 61 |
| ECH yield % | 65 | 60 | 58 |
| Ref. Ex. 8 | | | |

TABLE 18-continued

| Reaction time (hr) | 100 | 300 | 700 |
|---|---|---|---|
| HPO conversion % | 62 | 54 | 43 |
| ECH yield % | 56 | 49 | 39 |

EXAMPLE 18

Reaction was carried out in the same manner as in Example 10 except that methallyl chloride was used in place of the ALC and the weight ratio of the HPO to the methallyl chloride was set at 1 to 12.6 in Example 10. The results are given in Table 19.

REFERENCE EXAMPLE 9

Reaction was carried out in the same manner as in Example 18 except that calcium oxide was not used. The results are given in Table 19.

TABLE 19

| Reaction time (hr) | 100 | 300 | 700 |
|---|---|---|---|
| Example 18 | | | |
| HPO conversion % | 38 | 31 | 26 |
| 2-methyl ECH yield % | 34 | 28 | 23 |
| Ref. Ex. 9 | | | |
| HPO conversion % | 34 | 26 | 22 |
| 2-methyl ECH yield % | 31 | 23 | 20 |

What is claimed is:

1. A method for preparing an epichlorohydrin which comprises reacting allyl chloride or 2-alkylallyl chloride in which the alkyl radical has 1 to 3 carbon atoms with an alkyl hydroperoxide in the presence of a modified catalyst formed by substituting hydrocarbon groups, alkoxy groups, acyl groups, acyloxy groups, carbamoyloxy groups, amino groups or organosilyloxy groups for 1 to 50% of the silanol groups of a catalyst having titanium atoms and having on the same carrier 1 to 6 silanol groups per square nanometer thereof.

2. The method according to claim 1 wherein the hydrocarbon groups are methyl groups.

3. The method according to claim 1 wherein the alkoxy groups are methoxy groups.

4. The method according to claim 1 wherein the alkoxy groups are ethoxy groups.

5. The method according to claim 1 wherein the acyl groups are acetyl groups.

6. The method according to claim 1 wherein the acyloxy groups are acetoxyl groups.

7. The method according to claim 1 wherein the carbamoyloxy groups are N-phenylcarbamoyloxy groups.

8. The method according to claim 1 wherein the amino groups are dimethylamino groups.

9. The method according to claim 1 wherein the organosilyloxy groups are trimethylsilyloxy groups.

10. The method according to claim 1 wherein the reaction is carried out in the co-presence of a basic compound of an alkaline earth metal.

11. The method according to claim 1 wherein the reaction is carried out at a temperature in the range of 20° to 150° C.

12. The method according to claim 10, wherein said basic compound of an alkaline earth metal is an oxide, hydroxide, carbonate or organic acid salt of an alkaline earth metal.

13. The method according to claim 12, wherein said basic compound of an alkaline earth metal has the formula $MO$, $M(OH)_2$, $M(OH)X$, $MCO_3$ or $mX_2$, wherein M is Be, Mg, Ca, Sr or Ba, and X is a halogen atom.

14. The method according to claim 12, wherein said basic compound of an alkaline earth metal compound is calcium oxide.

15. The method according to claim 12, wherein said basic compound of an alkaline earth metal compound is barium carbonate.

16. The method according to claim 12, wherein said basic compound of an alkaline earth metal compound is calcium carbonate.

17. The method according to claim 12, wherein said basic compound of an alkaline earth metal compound is barium hydroxide.

18. The method according to claim 12, wherein said basic compound of an alkaline earth metal compound is magnesium hydroxide.

19. The method according to claim 12, wherein said basic compound of an alkaline earth metal compound is strontium oxide.

20. The method according to claim 12, wherein said basic compound of an alkaline earth metal compound is $MgCO_3 \cdot CaCO_3$.

21. The method according to claim 12, wherein the hydrocarbon groups are methyl groups.

22. The method according to claim 12 wherein the alkoxy groups are methoxy groups.

23. The method according to claim 12 wherein the alkoxy groups are ethoxy groups.

24. The method according to claim 12 wherein the acyl groups are acetyl groups.

25. The method according to claim 12 wherein the acyloxy groups are acetoxyl groups.

26. The method according to claim 12 wherein the carbamoyloxy groups are N-phenylcarbamoyloxy groups.

27. The method according to claim 12 wherein the amino groups are dimethylamino groups.

28. The method according to claim 12 wherein the organosilyloxy groups are trimethylsilyloxy groups.

29. The method according to claim 12 wherein the practice is carried out at a temperature in the range of 20° to 150° C.

* * * * *

UNITED STATES PATENT AND TRADEMARK OFFICE
CERTIFICATE OF CORRECTION

PATENT NO. : 5,011,953
DATED : April 30, 1991
INVENTOR(S) : TAKEHISA NAKANISHI ET AL It is certified that error appears in the above-identified patent and that said Letters Patent is hereby corrected as shown below:

In Claim 1, col. 17, line 38, after "atoms" insert

--bound to a silicon dioxide carrier via oxygen atoms--.

Signed and Sealed this

Sixteenth Day of November, 1993

Attest:

BRUCE LEHMAN

Attesting Officer

Commissioner of Patents and Trademarks